(12) United States Patent
Townsend et al.

(10) Patent No.: US 6,752,774 B2
(45) Date of Patent: Jun. 22, 2004

(54) TENSION ASSISTED ANKLE JOINT AND ORTHOTIC LIMB BRACES INCORPORATING SAME

(75) Inventors: Jeffrey Townsend, Bakersfield, CA (US); Steve Knecht, Bakersfield, CA (US)

(73) Assignee: Townsend Design, Bakersfield, CA (US)

( * ) Notice: Subject to any disclaimer, the term of this patent is extended or adjusted under 35 U.S.C. 154(b) by 121 days.

(21) Appl. No.: 09/876,074

(22) Filed: Jun. 8, 2001

(65) Prior Publication Data

US 2002/0188238 A1 Dec. 12, 2002

(51) Int. Cl.⁷ .................................................. A61F 5/00
(52) U.S. Cl. ............................. 602/16; 602/26; 602/27
(58) Field of Search ............................. 602/16, 27, 20, 602/21, 23, 26; 128/878, 882, 881; 623/51, 52, 55

(56) References Cited

U.S. PATENT DOCUMENTS

| | | | |
|---|---|---|---|
| 1,851,241 A | * | 3/1932 | Dresser |
| 2,267,848 A | * | 12/1941 | Talyor |
| 4,773,404 A | | 9/1988 | Townsend |
| 4,865,024 A | * | 9/1989 | Hensley et al. |
| 4,890,607 A | | 1/1990 | Townsend |
| 5,259,832 A | | 11/1993 | Townsend et al. |
| 5,330,418 A | | 7/1994 | Townsend et al. |
| 5,376,139 A | * | 12/1994 | Pitkin |
| 5,693,007 A | | 12/1997 | Townsend |
| 5,743,418 A | | 4/1998 | Ahrens |
| 5,908,398 A | | 6/1999 | DeToro |
| 6,102,881 A | | 8/2000 | Quackenbush et al. |
| 6,171,272 B1 | * | 1/2001 | Akita et al. |

* cited by examiner

Primary Examiner—Jerome W. Donnelly
(74) Attorney, Agent, or Firm—Nixon Peabody LLP; David S. Safran

(57) ABSTRACT

An improved limb brace joint includes a band that operates in tension to rotationally bias first and second longitudinal members of the joint. The band of the joint biases the rotation of the members to provide a dorsiflexion and/or plantarflexion assist when used in an ankle foot orthosis.

12 Claims, 8 Drawing Sheets

FIG. 8
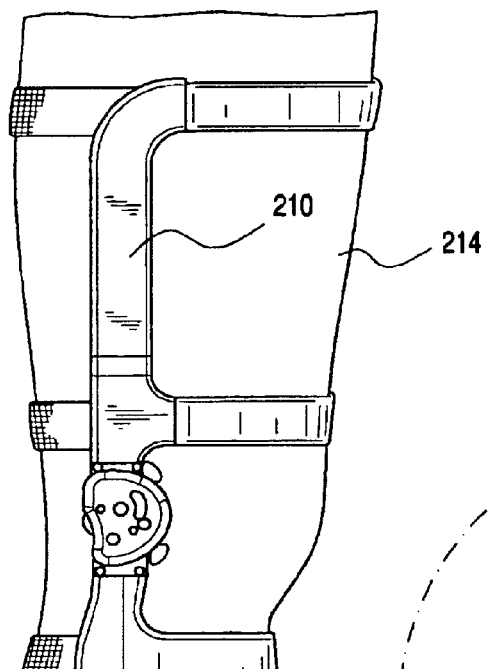
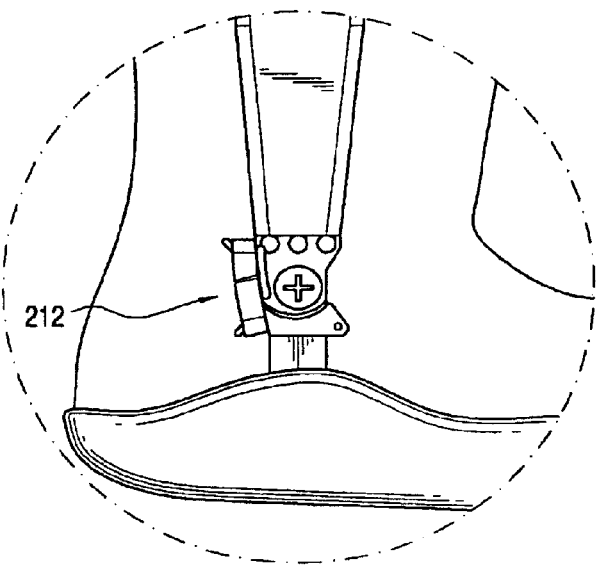
FIG. 9
FIG. 9

TENSION ASSISTED ANKLE JOINT AND ORTHOTIC LIMB BRACES INCORPORATING SAME

BACKGROUND OF THE INVENTION

1. Field of the Invention

The present invention is directed to the art of orthotic limb brace joints. In particular, the invention is directed to an improved limb brace joint that rotationally biases the limbs of the wearer.

2. Description of Related Art

Patients with physical conditions or injuries sometimes require the use of an orthotic limb brace, such as an ankle foot orthosis (AFO) or knee ankle foot orthosis (KAFO). These orthoses aid several functions in ambulation, including control of dorsiflexion and plantarflexion in both the stance and swing phases of gait. AFOs also stabilize the ankle in the frontal and transversal planes during balance and gait activities.

Some individuals are afflicted with a condition that does not permit the individual to have full control over muscles that raise and lower the foot. One condition for which an individual does not have full control over the muscles is known as "drop foot". "Drop foot" occurs when the individual has difficulty in raising the foot (dorsiflexion). Such a condition poses substantial difficulty when walking. The toe or ball of the foot often may not clear the ground while walking. As a result, the individual may end up dragging the foot or may find themselves tripping when walking. Therefore, the individual may stumble and fall while attempting to walk.

Various conventional devices attempt to remedy a drop foot condition by providing an L-shaped ankle and foot orthosis that biases the ankle joint such that the toe or ball portion of the foot is raised. For example, U.S. Pat. No. 5,908,398 to DeToro discloses an adjustable ankle and foot orthosis brace that includes an incrementally adjustable hinge assembly. Also, U.S. Pat. No. 6,102,881 discloses a hinged drop foot brace that Another conventional dorsiflexion assist ankle joint uses a ball bearing and a spring in a posterior channel of the ankle component that pushes against the posterior edge of the stirrup as the spring is compressed. The spring tension is varied by the use of a set screw at the top of the channel that compresses the spring. The spring must be loose enough to allow the foot to be flat on the floor after heel strike, but tight enough to prevent a foot "slap." The adjustment is also critical to produce enough dorsiflexion during the swing of the foot so that the foot clears the floor without dragging and potentially causing a fall. One problem with this design is that as the spring wears out during its use, it is necessary to continually increase the tension on the set screw. Eventually, the tension is increased to such a high level that the spring breaks inside the channel. The problem is that it is very difficult to repair and/or replace the spring. Additionally, it is impossible for the patient to repair the orthosis and a practitioner must be involved in the repair.

SUMMARY OF THE INVENTION

The inventors discovered that a joint is needed that provides for dorsiflexion assist and/or plantarflexion assist in a limb joint brace which is easily repairable by the patient. The joint of the invention solves this and other problems by providing for an easily repairable joint that assists in dorsiflexion and/or plantarflexion.

An exemplary embodiment of a joint in accordance with the invention includes a first longitudinal member rotationally hinged to a second longitudinal member and a band engaging each of the first and second longitudinal members in tension.

Another exemplary embodiment of a joint in accordance with the invention may include multiple bands on the same side of the joint or on opposite sides of the joint. The amount of assist may be adjusted by adding or removing bands and if bands are placed on both sides of the joint, a preferred position for the patient's limbs may be obtained by selecting bands which balance at the preferred rotational position.

The inventors also devised a band installation tool for the joint of the invention to provide for easy replacement of a faulty and/or failed band.

These and other features and advantages of this invention are described in or are apparent from the following detailed description of exemplary embodiments with reference to the accompanying drawings.

BRIEF DESCRIPTION OF THE DRAWINGS

FIG. 8 shows a second knee ankle foot orthosis incorporating the joint of FIG. 7 being worn by a patient;

FIG. 9 shows an enlarged detail view of the orthosis of FIG. 8;

DETAILED DESCRIPTION OF AN EXEMPLARY EMBODIMENT

Figure 1:
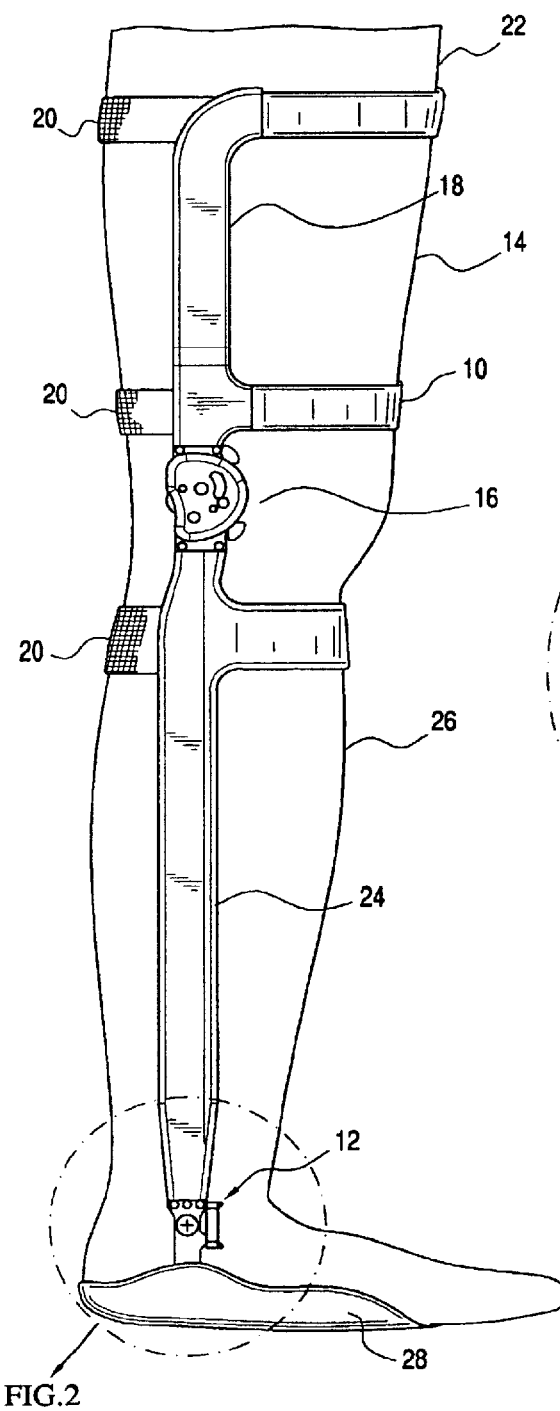
FIG. 1 is a side elevation view of a first knee ankle foot orthosis incorporating a first exemplary embodiment of the joint in accordance with the invention being worn by a patient.

FIG. 1 shows a knee ankle foot orthosis (KAFO) 10 that incorporates a first exemplary embodiment of a joint 12 in accordance with the invention being worn by a patient 14. The KAFO 10 has a solid core graphite shell that result in a rigid, durable bracing solution that achieves effective and consistent control. The KAFO 10 is ultra light, extremely low profile and exceptionally comfortable.

The KAFO 10 includes a second joint 16 positioned proximate to the knee and may also incorporate the features of the invention. However, joint 16 may be of known design as well, such as those disclosed in U.S. Pat. Nos. 4,773,404; 4,890,607; 5,259,832; 5,330,418; and 5,743,418 and commonly owned, co-pending U.S. patent application Ser. No. 09/694,484.

Figure 2:
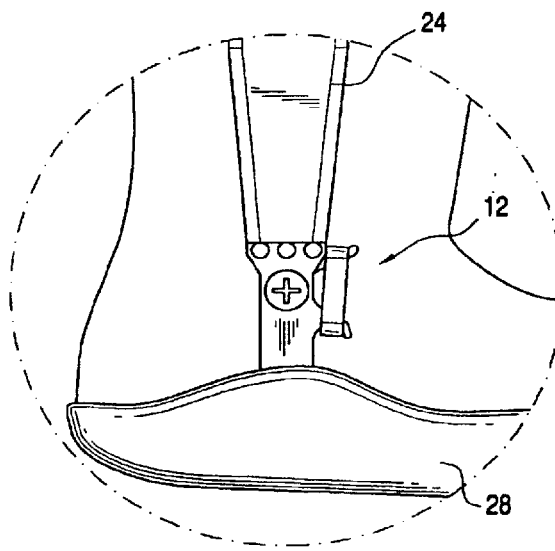
FIG. 2 is an enlarged view of encircled detail A of FIG. 1.

FIG. 2 shows an enlarged detail view of the joint 12. The KAFO includes a thigh shell 18 and two straps or bands 20 holding the thigh shell 18 to the thigh 22 of the patient 14. The KAFO also includes a below knee shell 24 which is held onto the lower leg 26 of the patient 14 using bands 20. Lastly, the KAFO includes a foot plate 28 connected to the below knee shell 24 using the joint 12. The thigh shell (femoral strut) 18, below knee shell (tibial strut) 24 and the foot plate 28 are molded to the shape of the patient for comfort. Such molding techniques are known and by themselves form no part of this invention; see, U.S. Pat. No. 5,693,007.

Figure 3:
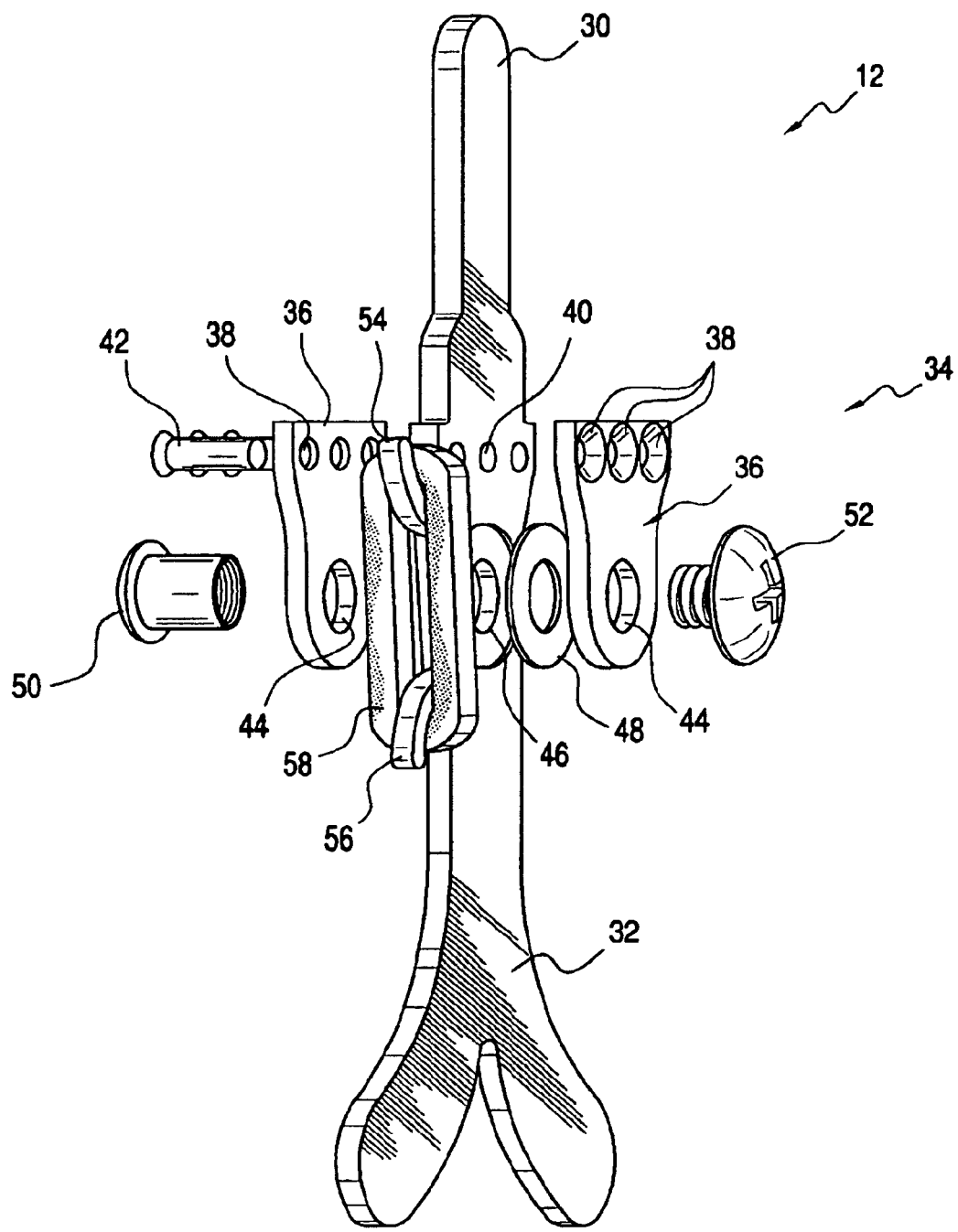
FIG. 3 is an exploded assembly view of the ankle joint of FIG. 1.
Figure 4:
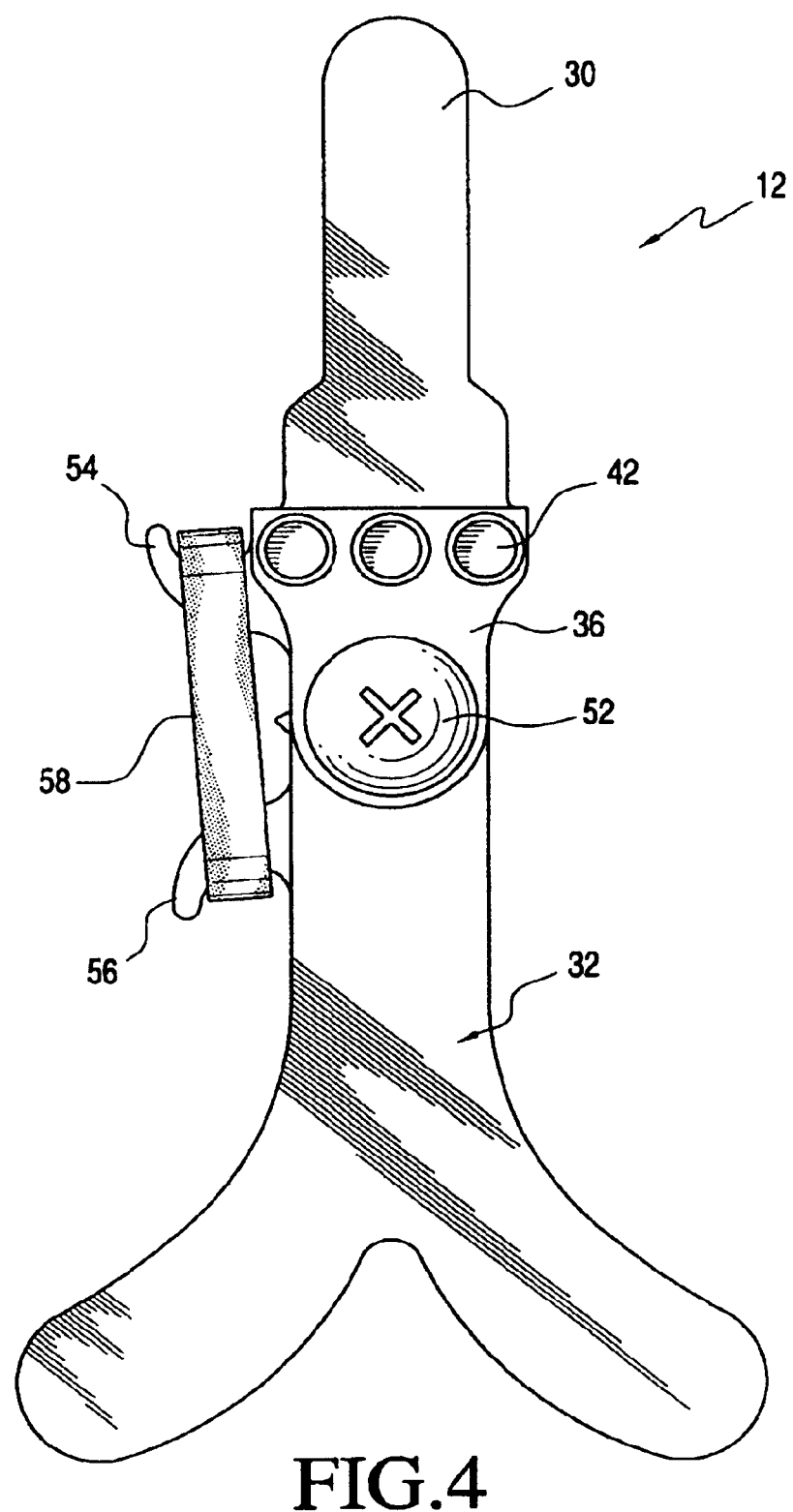
FIG. 4 is a side view of the joint of FIG. 1.
Figure 10:
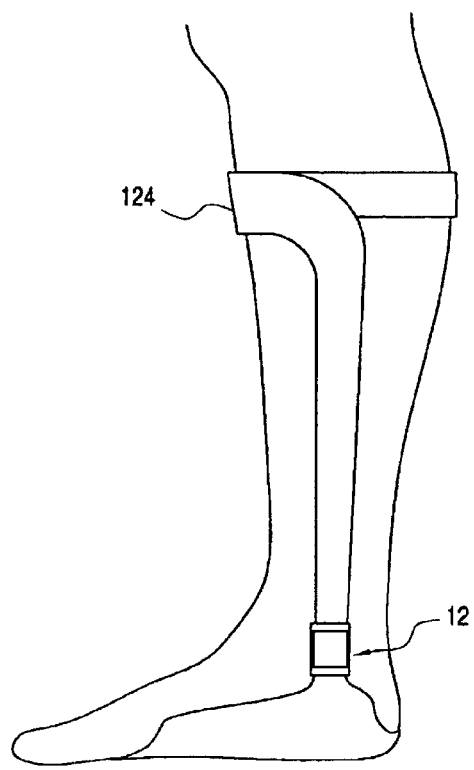
FIG. 10 shows an ankle foot orthosis with an anterior pre-tibial band in accordance with the invention.
Figure 11:
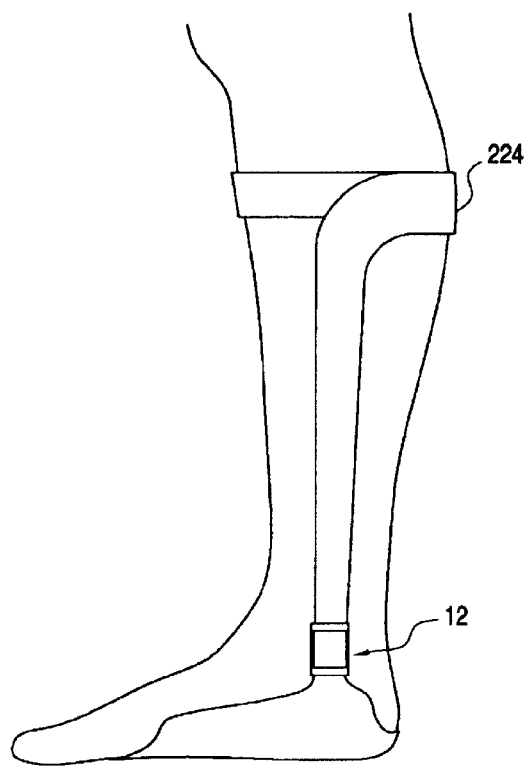
FIG. 11 shows an ankle foot orthosis with a posterior proximal band in accordance with the invention.

The first exemplary embodiment of the joint 12 is shown in FIG. 3 in an exploded assembly view and in FIG. 4 in an assembled side view. The joint 12 is shown disconnected from the below knee shell 24 and the foot plate 28 for purposes of explanation and to represent the fact that the joint 12 can be a separate component from the KAFO 12 that be used with other types of KAFOs or as part of an ankle foot orthosis (AFO), e.g., with an anterior pre-tibial band 124 (FIG. 10) or a posterior proximal band 224 (FIG. 11), or even incorporated into therapeutic footwear to name just a few of the various options available for use of the joint 12.

The joint 12 includes a first longitudinal member 30 connected to a second longitudinal member 32 by a hinge 34. The hinge 34 includes a pair of side plates 36. Each side plate 36 includes rivet receiving holes 38 which match rivet receiving holes 40 on the first longitudinal member 30. Rivets 42 extend through the rivet receiving holes of each side plate 36 and the first longitudinal member 30. The side plates 36 each include a truss rivet receiving hole 44 that aligns with a matching truss rivet receiving hole 46 in the second longitudinal member 32. The side plates 36 enclose portions of the first longitudinal member 30, the second longitudinal member 32 and a pair of washers 48. A truss rivet 50 extends through the truss rivet receiving holes 44, 46 and receives a truss screw 52. The first longitudinal member 30 and second longitudinal member 32 rotate relative to each other about a central axis of the truss rivet 50. Of course the male and female configurations of the ends of members 30, 32 could be reversed and then the side plates would be mounted to the member 32 instead of the side member 30.

The first longitudinal member 30 also includes an upwardly extending band receiving hook 54 and the second longitudinal member includes a downward extending band receiving hook 56. A latex band 58 extends around the hooks 54 and 56 and acts in tension to try to bring the two hooks 54 and 56 together.

Figure 5:
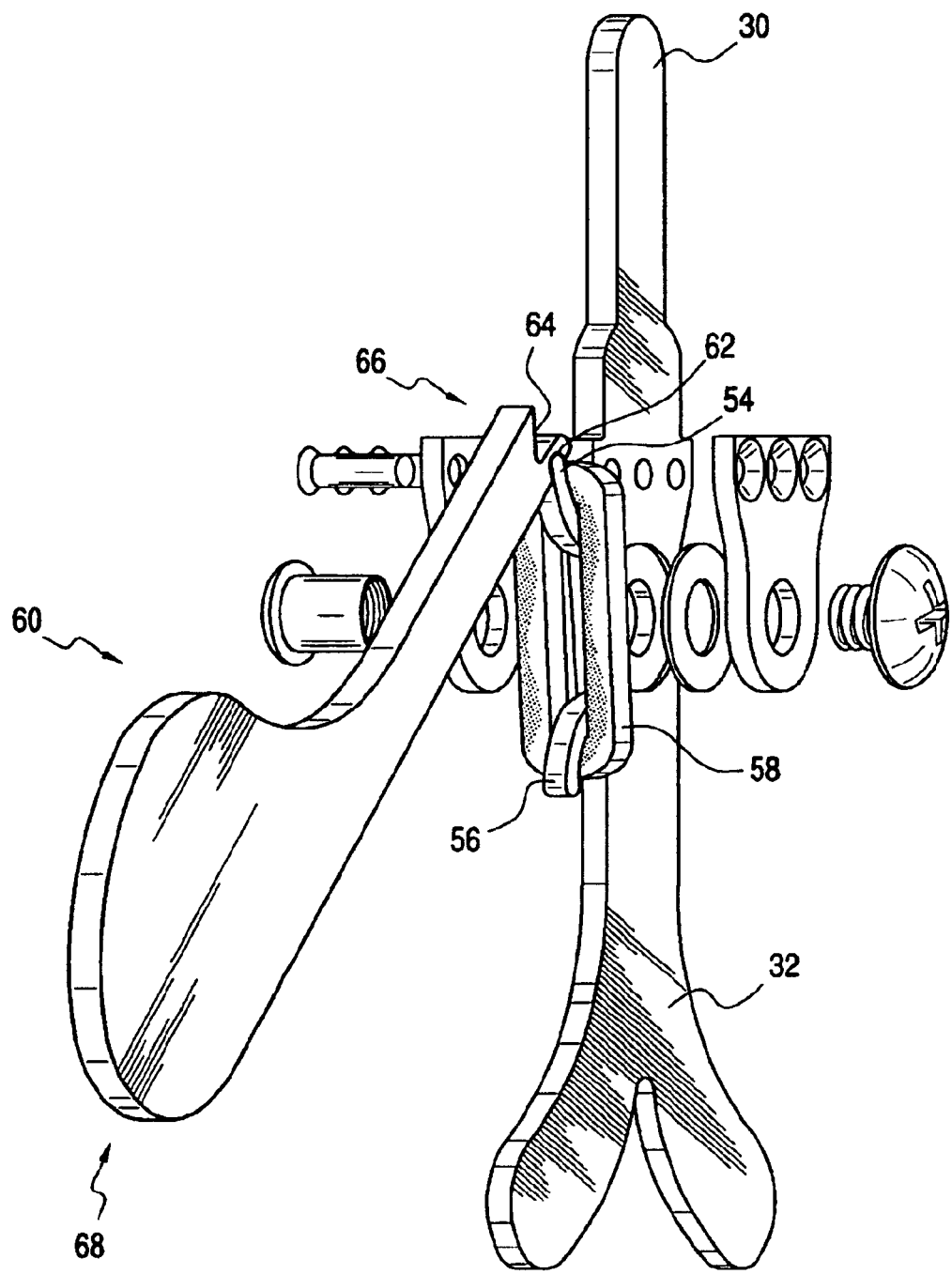
FIG. 5 is an exploded assembly view of the joint of FIG. 1 and a band installation tool.

Should the latex band 58 fail, the patient may easily replace the band 58 using a band application tool 60, an example of which is shown in FIG. 5. The band application tool 60 includes a hook receiving notch 62 and a band receiving platform 64 at a proximal end 66. The band application tool 60 operates by placing a replacement band 58 around the hook 56 on the second longitudinal member 32 and around the band receiving platform 64. The user then positions the hook receiving notch 62 on the hook 54 on the first longitudinal member 30 and rotates the distal end 68 of the tool 60 upwardly until the band 58 transfers to the hook 54 on the first longitudinal member 30.

As shown in FIGS. 1 & 2, the latex band, the hooks 54, 56 and the latex band 58 are positioned anterior to the truss rivet 50 such that the band 58 operates to assist in the dorsiflexion of the foot of the patient 14. Although not shown in this drawing, it is understood that the hooks 54, 56 and the latex band 58 may be positioned posterior to the truss rivet 50 to provide plantarflexion assist in the manner shown for joint 212 in FIG. 8.

Figure 6:
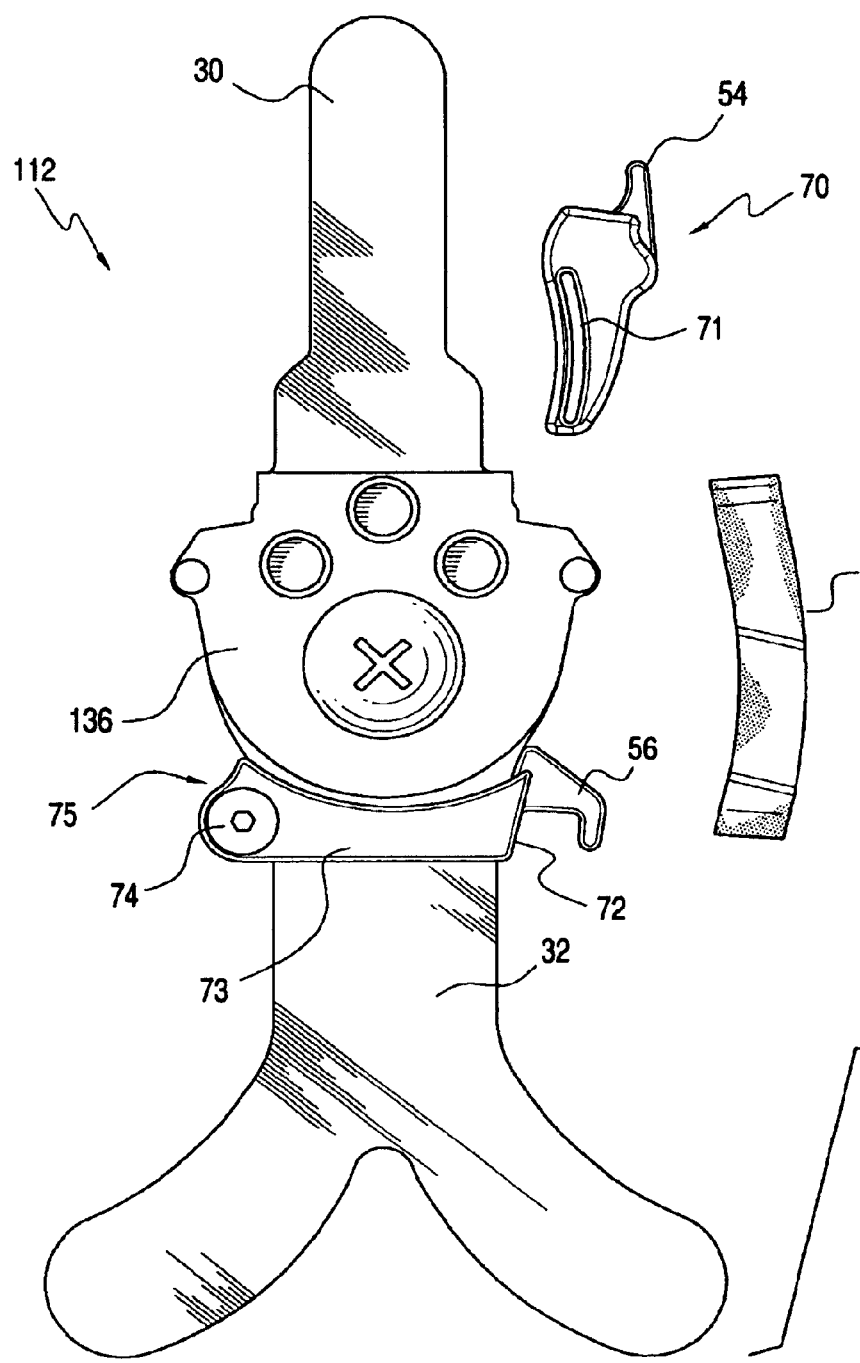
FIG. 6 is a partially exploded view of a second exemplary embodiment of the joint in accordance with the invention.

FIG. 6 show the details of a second exemplary embodiment of a joint 112 in accordance with the invention. The joint 112 of FIG. 6 is similar to the joint 12 shown in FIGS. 1–5 except that the joint 112 is a double adjustable joint. The joint 112 is double adjustable because the range of rotation is adjustable in both rotation directions. The joint 112 adjusts the limit of rotation by including a stop (not shown) on the second longitudinal member that abuts an adjustable stop screw (not shown) that is captured between the side plates 136 that are connected to the first longitudinal member. This ability to adjust the limit of rotation is known in the art. However, the joint 112 is unique in that it incorporates the features of the invention to provide for dorsiflexion and/or plantarflexion assist.

The joint 112 includes an upper assist 70 and a lower assist 72. The upper assist 70, the lower assist 72 and the band 58 transform the conventional double adjustable joint 112 into a double adjustable joint which includes an assist function. The upper assist 70 incorporates an upwardly extending band receiving hook 54 and is adapted to surround a portion of the side plates 136. The upper assist 70 also includes a band guide 71 that prevents the band 58 from interfering with the motion of the joint. The lower assist 72 includes two longitudinally extending prongs 73 that extend from a proximal end having a downward extending band receiving hook 56 to a distal end having a screw receiving portion 75. The lower assist 72 is clamped in position on the second longitudinal member 32 using a clamping screw 74 that engages the screw receiving portions 75 of the two longitudinally extending prongs 73.

Figure 7:
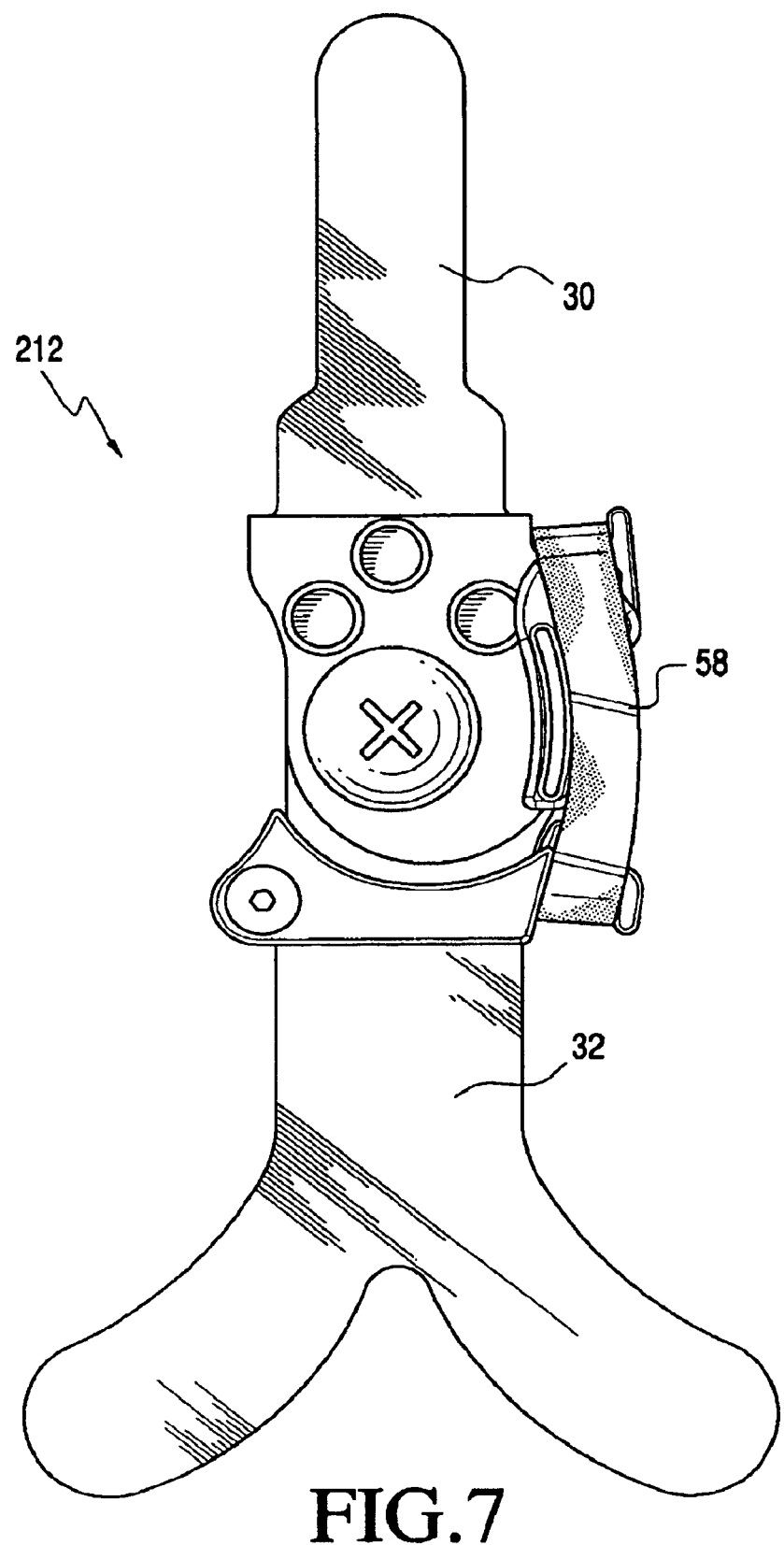
FIG. 7 shows a plan view of an assembled third exemplary embodiment of a joint in accordance with the invention.

FIG. 7 shows a side view of a third exemplary embodiment of a joint 212 in accordance with the invention. Similar to the joint 112 of FIG. 6, the joint 212 of FIG. 7 has an upper assist 70 and a lower assist 72. However, the joint 212 is a single adjustable joint. The single adjustable joint 212 may be adjusted to limit the rotation in only one direction. For example, the rotational range of the second longitudinal member 32 of the joint 212 is limited in the counterclockwise direction relative to the first longitudinal member 30 as shown in FIG. 7. Additionally, the band 58 pulls the second longitudinal member 32 in the counterclockwise direction relative to the first longitudinal member 30.

FIGS. 8 & 9 show the joint 212 incorporated into a second exemplary embodiment of a knee ankle foot orthosis 210 being worn by a second patient 214. In contrast to the joint 12 incorporated into the knee ankle foot orthosis 10 of FIGS. 1 & 2, which is designed to assist in dorsiflexion, the band 58 of the joint 212 on the KAFO 210 of FIGS. 8 & 9 is positioned posterior to the joint so that the joint assists in plantarflexion.

While the exemplary joints described above were all in relation to a knee ankle foot orthosis, it is understood that the joint of the invention may be used in any type of orthosis where an assist may be useful. For example, the joint may be used on an ankle foot orthosis, such as those shown in FIGS. 10 & 11, an arm orthosis and the like. Additionally, while the joint is currently adapted for incorporation into a carbon fiber/foam core strut brace using either a wet layup lamination, or pre-preg heat cured technique, it is understood that the joint of the invention may be incorporated into any type of orthosis, such as a typical side bar brace. The application or use of the joint of the invention is not limited by this specification.

It is also to be understood that the inventive features of the joint of the invention may be incorporated into any type of joint. As shown above, the features of the invention may be incorporated into a non-adjustable joint as shown in FIGS. 1–4, a double adjustable joint as shown in FIG. 6 or a single-adjustable joint as shown in FIGS. 7–9.

Additionally, it is understood that the bands of the invention may be made from any material that generally operates in tension. For example, the bands of the invention may be made from latex rubber and the like. The bands may also be made available with different levels of tensile strength or of a different durometer measurement to provide a predetermined level of assist to the joint. Also, multiple bands may be used to vary the tension.

Lastly, while the exemplary embodiments of the joint of the invention described above provide assist in only one direction, it is understood that the joint of the invention may include bands on both sides of the joint to provide an assist in both rotation directions. Such a joint may have the strength of the bands and the positions of the hooks designed such that the joint has a preferred position in which the tension on each side of the joint is substantially balanced. An embodiment of the joint of the invention having a double assist may provide for a preferred rotational position between the limbs of a patient and will assist the patient in returning the limb to that position regardless of the rotational direction.

While this invention has been described in conjunction with the specific embodiments outlined above, it is evident that many alternatives, modifications and variations are apparent to those skilled in the art. Accordingly, the exemplary embodiments of the invention as set forth above are intended to be illustrative and not limiting. Various changes may be made without departing from the spirit and scope of the invention.

What is claimed is:

1. A joint for an orthosis, comprising
    a first longitudinal member;
    a second longitudinal member rotationally hinged to the first longitudinal member;
    at least one band engaging the first longitudinal member and the second longitudinal member in tension;
    a pair of side plates fixed to the first longitudinal member and forming a portion of a hinge rotationally connecting the second longitudinal member to the first longitudinal member;
    an upper assist engaging the pair of side plates and forming a first band receiving hook for the first longitudinal member; and
    a lower assist engaging the second longitudinal member and forming a second band receiving hook for the second longitudinal member, wherein the band engages the first and second band receiving hooks.

2. The joint of claim 1, wherein the upper assist engages each of the pair of side plates by surrounding a portion of each of the pair of side plates.

3. The joint of claim 1, wherein the upper assist includes a band guide.

4. The joint of claim 1, wherein the lower assist includes two longitudinal prongs that surround a portion of the second longitudinal member, wherein each prong has a distal end and a proximal end, wherein the lower assist includes a band receiving hook at the proximal end and a screw receiving portion at the distal end, wherein the lower assist further includes a screw engaging the screw receiving portions of the two longitudinal prongs to clamp the lower assist to the second longitudinal member.

5. An orthosis comprising:
    a first limb engaging member;
    a first longitudinal member engaging the first limb engaging member;
    a second longitudinal member rotationally hinged to the first longitudinal member;
    a second limb engaging member engaging the second longitudinal member;
    a band engaging the first longitudinal member and the second longitudinal member;
    a pair of side plates fixed to the first longitudinal member forming a portion of a hinge rotationally connecting the second longitudinal member to the first longitudinal member;
    an upper assist engaging the pair of side plates and forming a first band receiving hook for the first longitudinal member; and
    a lower assist engaging the second longitudinal member and forming a second band receiving hook for the second longitudinal member, wherein the band engages the first and second band receiving hooks.

6. The orthosis of claim 5, wherein the band is positioned posterior to the hinge between the first and second longitudinal members.

7. The orthosis of claim 5, wherein the band is positioned anterior to the hinge between the first and second longitudinal members.

8. The orthosis of claim 5, wherein the upper assist engages each of the pair of side plates by surrounding a portion of each of the pair of side plates.

9. The orthosis of claim 5, wherein the upper assist includes a band guide.

10. The orthosis of claim 5, wherein the lower assist includes two longitudinal prongs that surround a portion of the second longitudinal member, wherein each prong has a distal end and a proximal end, wherein the lower assist includes a band receiving hook at the proximal end and a screw receiving portion at the distal end, wherein the lower assist further includes a screw engaging the screw receiving portions to clamp the lower assist to the second longitudinal member.

11. The orthosis of claim 5, wherein the orthosis is a knee ankle foot orthosis; wherein one of said limb engaging members is a foot plate and the other of said limb engaging members is a tibial strut having at least one lower leg engaging band, said tibial strut being connected, via knee joint mechanism, to a femoral strut having at least one upper leg engaging band.

12. The orthosis of claim 5, wherein the orthosis is an ankle foot orthosis;
    wherein one of said limb engaging members is a foot plate and the other of said limb engaging members is a tibial strut having at least one lower leg engaging band.

* * * * *